United States Patent [19]

Groenhof

[11] 4,198,190
[45] Apr. 15, 1980

[54] VAPOR BOOSTER FLUIDS

[75] Inventor: Eugene D. Groenhof, Freeland, Mich.

[73] Assignee: Dow Corning Corporation, Midland, Mich.

[21] Appl. No.: 935,273

[22] Filed: Aug. 21, 1978

[51] Int. Cl.$^2$ ............................................. F04F 9/00
[52] U.S. Cl. .................................................... 417/55
[58] Field of Search ..................... 417/55, 152–154; 260/448.2 R

[56] References Cited

U.S. PATENT DOCUMENTS

| 2,469,889 | 5/1949 | Wilcock et al. | 417/55 X |
| 2,530,356 | 11/1950 | Hunter | 260/448.2 R |
| 2,951,629 | 9/1960 | Shepardson | 417/55 |

FOREIGN PATENT DOCUMENTS

| 2195276 | 3/1974 | France | 417/55 |
| 514121 | 10/1976 | U.S.S.R. | 417/55 |

*Primary Examiner*—Carlton R. Croyle
*Assistant Examiner*—Edward Look
*Attorney, Agent, or Firm*—Jack E. Moermond

[57] ABSTRACT

A vapor booster diffusion pump is provided with an organosiloxane pump fluid consisting essentially of octamethyl-3,5-diphenyltetrasiloxane.

1 Claim, No Drawings

VAPOR BOOSTER FLUIDS

BACKGROUND OF THE INVENTION

The present invention relates generally to production of high vacua and more particularly to improved organosilicon fluids for use in vapor booster diffusion pumps.

Vapor booster pumps are a variety of diffusion pumps specifically constructed for use in such diverse technologies as vacuum metallurgy, food processing, distillation, environmental simulation, vacuum coating, cathode ray tube evacuation, and the like, where it is desired that large quantities of gas be pumped at vacuums in a range somewhat lower than those employed [i.e., $10^{-6}$ to $10^{-8}$ torr. (untrapped) and $10^{-10}$ to $10^{-11}$ (trapped)] in diffusion pumps of a general construction. Manufacturers of such pumps ordinarily specify that they be operated with fluids capable of developing ultimate vacuums "better than $10^{-4}$ torr." or at least within the range of $1 \times 10^{-4}$ to $5 \times 10^{-4}$ torr. Additional characteristics desired in fluids for use in vapor booster pumps include: resistance to thermal oxidation (thus avoiding the need for pump cooling before the vacuum is released); resistance to decomposition into chemical by-products which reduce ultimate vacuum (thus avoiding the need for frequent fluid replacement); and, nonreactivity with metal parts, elastomeric seals, hydrogen and carbon monoxide gases. The ongoing search for fluids possessing the above-noted characteristics has continued over the years.

The use of organopolysiloxanes and silahydrocarbons as diffusion pump fluids has been known since approximately 1945. Among the compounds of interest to the background of the present invention are phenylmethylsiloxanes and particularly low molecular weight ogligomers. U.S. Pat. No. 2,530,356 discloses diffusion pump fluid usages for a large number of such compounds having a boiling point of 250°-500° C. at atmospheric pressure. U.S. Pat. No. 2,567,110, as another example, discloses the preparation of a variety of phenylmethyl siloxanes, including mixtures of siloxanes of the formula;

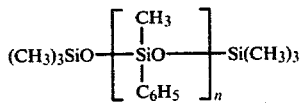

wherein n has an average value of 4. Such fluids were noted to have a boiling point greater than 200° C. at 1 mm.Hg. and were therefore proposed as having utility as diffusion pump fluids. The use as diffusion pump fields of other, lower molecular weight, phenylmethylsiloxanes as diffusion pump fluids is noted in U.S. Pat. No. 2,890,234. That reference discloses the preparation and use of both 1,3,3,5-tetraphenyl-1,1,5,5-tetramethyltrisiloxane and 1,3,5-triphenyl-1,1,3,5,5-pentamethyltrisiloxane as diffusion pump fluids.

Despite the above-noted interest in relatively low molecular weight phenylmethylsiloxanes (hexasiloxanes in U.S. Pat. No. 2,567,110 and trisiloxanes in U.S. Pat. No. 2,890,234), proposals for use of phenylmethyltetrasiloxanes and phenylmethylpentasiloxanes are conspicuously absent from the art pertaining to diffusion pump fluids. This is likely due in part to the fact that their reported boiling points are rather low. Low boiling points generally indicate that the particular fluid is too volatile and therefore too difficult to condense at high vapor operation. More significantly, the reported vapor pressures of these siloxanes are such as would make them appear to be of little use in diffusion pumps. V.E. Ditsent, et al., reporting on the vapor pressures of alpha-omega hexamethylpolymethylphenylsiloxanes in the *Russian Journal of Physical Chemistry*, 45 (6), (1971), reported the A and B coefficients for the vapor pressure of nonamethyl-3,5,7-triphenylpentasiloxane as 9.1545 and 4124, respectively. The calculated ultimate vacuum at 25° C. for such a compound, using the equation log $P = A - B/T$ generates, log $P = 9.1545 - (4124/298.2) = -4.6751$ $P = 0.000021$ or $2.11 \times 10^{-5}$ torr.

The A and B coefficients for the vapor pressure of octamethyl-3,5-diphenyltetrasiloxane reported by Ditsent, et al, are 8.8435 and 3543 respectively. Again applying log $P = A - B/T$ for calculation of the ultimate pressure, there is generated log $P = 8.8435 - (3543/298.2) = 3.03779$ $P = 0.00092$ or $9.2 \times 10^{-4}$ torr.

Such an ultimate vacuum value is nearly one order of mangitude removed from manufacturers' recommendations of $10^{-4}$ torr. for vapor booster pump fluids and indicates that the tetrasiloxane would be useless in vapor booster pumps.

BRIEF SUMMARY

The present invention provides an improvement in a method wherein a system is evacuated by a vapor booster diffusion vacuum pump, said improvement comprising the step of entraining gas in a stream of vapors of an organosilicon fluid consisting essentially of octamethyl-3,5-diphenyltetrasiloxane. Such a fluid has remarkably good thermal stability, resistance to decomposition, and non-reactivity with pump components and gases. It is quite useful despite its low boiling point (130°-140° C. at 1 mm.Hg.) and possesses ultimate vacuum characteristics far in excess of those predictable from prior art measurements of its properties.

Numerous aspects and wholly unexpected advantages of the invention will become apparent upon consideration of the following detailed description.

DETAILED DESCRIPTION

The following example illustrates a suitable method for the preparation of octamethyl-3,5,-diphenyltetrasiloxane.

EXAMPLE 1

Phenylmethylsiloxane hydroylzate (2176 g.) having the general formula,

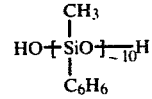

was equilibriated with 1300 g. of hexamethyldisiloxane in the presence of 174 g. Ansul ® 141 diethylene glycol dimethyl ether and 3.5 g. of potassium hydroxide. The mixture was refluxed at 80° to 125° C. for 24 hours through a Dean Stark trap which removed 51 ml. water. A sweep of helium gas was maintained at the top of the condenser to prevent neutralization of the catalyst during the reaction. Gas liquid chromatography (GLC) analysis showed the reaction to be complete. The base was neutralized with trimethylchlorosilane (7.6 ml.) and then 17 g. of sodium hydroxide was added. The product was the vacuum distilled through a pear-shaped stripping head into a fraction cutter at a pressure of about 2 mm.Hg. Four distillation cuts were taken and analyzed by GLC. Cut No. 3, an 888 g. portion distilling between 132° C. and 1.75 mm.Hg. and 177° C. at 2.00 mm.Hg., contained the predominant portion of the desired linear tetramer in about 75% pure form. Small amounts of the tetramer in the second and fourth cuts brought the total conversion to about 20 percent.

The following example illustrates certain of the properties of octamethyl-3,5-diphenyltetrasiloxane.

EXAMPLE 2

Octamethyl-3,5-diphenyltetrasiloxane prepared according to the method of Example 1 was subjected to physical analysis and revealed the following properties:

| Property | Limits |
| --- | --- |
| Viscosity at 77° F. | 6.13 |
| Viscosity at 100° F. | 4.66 |
| Viscosity at 210° F. | 1.84 |
| Specific gravity at 25° C. | 0.974 |
| Refractive Index at 25° C. | 1.4748 |
| Flash Point | 300° F. |
| Freeze Point | −40° C. |
| Acid No. | 0.01 (max.) |
| Surface Tension | 24.2 dynes/cm. |

The performance of octamethyl-3,5-diphenyltetrasiloxane of Example 1 as a diffusion pump fluid was evaluated in a single-stage, glass diffusion pump over a range of pressure of from $1 \times 10^{-4}$ to about $2 \times 10^{-6}$ torr. The fluid was placed in the apparatus which was then run for about 20 hours. The pressure in the system was then measured with a Knudsen torsion-vane gauge, with the lowest pressure measured over a range of heater inputs defined as the ultimate vacuum. The reported ultimate pressure for this fluid was a remarkable $4.9 \times 10^{-5}$. This was over one order of magnitude greater than could be predicted from prior art reports of its characteristics and well within the recommended limits for use in vapor booster pumps.

The following example illustrates vapor booster pump fluid characteristics for octamethyl-3,5-diphenyltetrasiloxane in comparison to high quality commercial booster pump fluid.

EXAMPLE 3

Using a Stokes Ring Jet Pump, throughput data for octamethyl-3,5-diphenylterrasiloxane was obtained and compared to that of Arochlor ® polychlorinated biphenyl vapor booster pump fluid at an inlet pressure of 25 microns. The following table provides the comparative data.

Table 1

| Heat Input, kw | Throughput as Percentage of Arochlor Throughput, 18 Kw |
| --- | --- |
| 9 | 66 |
| 10.8 | 66–7 |
| 12 | 66 |
| ~16 | 75 |
| ~18 | 77 |

This data compares favorably with, for example, other commercial pump fluids such as Invoil 40 ® hydrocarbon oil which has 40–45% of Arochlor's throughput under the same conditions.

Modifications and variations of the invention as disclosed above are expected to occur to those skilled in the art. As an example, it is fully expected that alternative methods will be developed for producing octamethyl-3,5-diphenyltetrasiloxane in higher yields having a greater degree of purity. Only the limitations appearing in the appended claims should be placed thereon.

What is claimed is:

1. In a method wherein a system is evacuated by a vapor booster diffusion vacuum pump, the improvement comprising entraining gas in a stream of vapors of an organosilicon fluid consisting essentially of octamethyl-3,5-diphenyltetrasiloxane.

* * * * *